(12) United States Patent
Kuroda et al.

(10) Patent No.: US 11,517,359 B2
(45) Date of Patent: Dec. 6, 2022

(54) BONE PLATE AND BONE PLATE KIT

(71) Applicant: OLYMPUS TERUMO BIOMATERIALS CORP., Tokyo (JP)

(72) Inventors: Koichi Kuroda, Tokyo (JP); Yasuharu Yokoyama, Tokyo (JP); Tomohiko Fukuhara, Tokyo (JP); Masaki Atarashi, Tokyo (JP); Kitaru Suzuki, Tokyo (JP); Minoru Harada, Tokyo (JP); Toshihisa Iwanaga, Tokyo (JP); Mitsuya Urata, Tokyo (JP)

(73) Assignee: OLYMPUS TERUMO BIOMATERIALS CORP., Tokyo (JP)

( * ) Notice: Subject to any disclaimer, the term of this patent is extended or adjusted under 35 U.S.C. 154(b) by 69 days.

(21) Appl. No.: 17/116,306

(22) Filed: Dec. 9, 2020

(65) Prior Publication Data
US 2021/0177473 A1   Jun. 17, 2021

Related U.S. Application Data

(63) Continuation of application No. PCT/JP2019/022994, filed on Jun. 10, 2019.
(Continued)

(51) Int. Cl.
*A61B 17/80* (2006.01)
*A61B 17/86* (2006.01)

(52) U.S. Cl.
CPC ...... *A61B 17/8014* (2013.01); *A61B 17/8057* (2013.01); *A61B 17/8605* (2013.01)

(58) Field of Classification Search
CPC ................................................ A61B 17/8014
See application file for complete search history.

(56) References Cited

U.S. PATENT DOCUMENTS

| 4,683,878 A | 8/1987 | Carter |
| 6,533,786 B1 | 3/2003 | Needham et al. |

(Continued)

FOREIGN PATENT DOCUMENTS

| CA | 2398372 | 8/2001 |
| CA | 2367085 | 9/2001 |

(Continued)

OTHER PUBLICATIONS

Extended European Search Report dated Feb. 22, 2022 received in 19818543.1.

(Continued)

*Primary Examiner* — Olivia C Chang
(74) *Attorney, Agent, or Firm* — Scully, Scott, Murphy & Presser, P.C.

(57) ABSTRACT

In order to apply, with a simple and easy means, proper pressure between bone segments spaced apart as a result of osteotomy or a bone fracture, without lowering the fixing force at the screw meshing portion, without increasing a dead space, and without increasing the thickness of the plate, the present invention provides a bone plate having an upper face, which is to be in contact with bone, a lower face, which is to be in contact with the bone, and a plurality of holes arranged to receive bone screws and connecting the upper face and the lower face. In at least one of the holes, a portion of an edge, on the upper face, of the hole is formed so as to be raised in the form of a protrusion higher than the upper face around the hole.

8 Claims, 5 Drawing Sheets

Related U.S. Application Data

(60) Provisional application No. 62/683,669, filed on Jun. 12, 2018.

(56) References Cited

U.S. PATENT DOCUMENTS

| | | |
|---|---|---|
| 2002/0045901 A1 | 4/2002 | Wagner et al. |
| 2002/0120273 A1 | 8/2002 | Needham et al. |
| 2002/0183752 A1 | 12/2002 | Steiner et al. |
| 2004/0181228 A1 | 9/2004 | Wagner et al. |
| 2004/0236332 A1 | 11/2004 | Frigg |
| 2005/0070904 A1 | 3/2005 | Gerlach et al. |
| 2006/0095044 A1 | 5/2006 | Grady et al. |
| 2007/0203492 A1 | 8/2007 | Needham et al. |
| 2008/0015593 A1 | 1/2008 | Pfefferle et al. |
| 2008/0132955 A1 | 6/2008 | Frigg |
| 2008/0161860 A1 | 7/2008 | Ahrens et al. |
| 2009/0088768 A1 | 4/2009 | Grant et al. |
| 2009/0088804 A1 | 4/2009 | Kyle et al. |
| 2009/0088805 A1 | 4/2009 | Leyden et al. |
| 2009/0088806 A1 | 4/2009 | Leyden et al. |
| 2010/0082069 A1 | 4/2010 | Wolter |
| 2010/0137873 A1 | 6/2010 | Grady, Jr. et al. |
| 2010/0145397 A1 | 6/2010 | Overes et al. |
| 2010/0312280 A1 | 12/2010 | Overes et al. |
| 2011/0009866 A1 | 1/2011 | Johnson et al. |
| 2011/0295325 A1 | 12/2011 | Wagner et al. |
| 2012/0022600 A1 | 1/2012 | Overes et al. |
| 2012/0265255 A1 | 10/2012 | Hilse et al. |
| 2013/0150900 A1 | 6/2013 | Haddad et al. |
| 2014/0039497 A1 | 2/2014 | Overes et al. |
| 2014/0163622 A1 | 6/2014 | Haddad et al. |
| 2015/0119943 A1 | 4/2015 | Milella, Jr. et al. |
| 2015/0142055 A1 | 5/2015 | Overes et al. |
| 2015/0164565 A1 | 6/2015 | Johnson et al. |
| 2015/0201981 A1 | 7/2015 | Hilse et al. |
| 2015/0201983 A1 | 7/2015 | Ahrens et al. |
| 2015/0272635 A1 | 10/2015 | Overes et al. |
| 2017/0071645 A1 | 3/2017 | Haddad et al. |
| 2017/0128111 A1 | 5/2017 | Johnson et al. |
| 2017/0348030 A1 | 12/2017 | Haddad et al. |
| 2018/0161080 A1 | 6/2018 | Johnson et al. |
| 2019/0142477 A1* | 5/2019 | Wolfe ................ A61B 17/8605 606/280 |
| 2019/0314067 A1 | 10/2019 | Johnson et al. |

FOREIGN PATENT DOCUMENTS

| | | |
|---|---|---|
| CN | 101355911 A | 1/2009 |
| CN | 101653368 A | 2/2010 |
| CN | 101668491 A | 3/2010 |
| CN | 105125270 A | 12/2015 |
| CN | 105147376 A | 12/2015 |
| CN | 206381233 U | 8/2017 |
| EP | 2368506 A1 | 9/2011 |
| EP | 2954862 A1 | 12/2015 |
| EP | 3446651 A1 | 2/2019 |
| JP | 2002-537937 A | 11/2002 |
| JP | 2003-521303 A | 7/2003 |
| JP | 2007-507296 A | 3/2007 |
| JP | 4121141 B2 | 7/2008 |
| JP | 4162408 B2 | 10/2008 |
| JP | 2009-520528 A | 5/2009 |
| JP | 2011-010792 A | 1/2011 |
| JP | 2011-189174 A | 9/2011 |
| JP | 2012-502760 A | 2/2012 |
| JP | 2012-510875 A | 5/2012 |
| JP | 4979712 B2 | 7/2012 |
| JP | 5198623 B2 | 5/2013 |
| JP | 2019-037782 A | 3/2019 |
| TW | 201340931 A | 10/2013 |
| TW | 202000140 A | 1/2020 |
| WO | 01/26566 A1 | 4/2001 |
| WO | 2005/032386 A1 | 4/2005 |
| WO | 2006/050507 A1 | 5/2006 |
| WO | 2009/042510 A2 | 4/2009 |
| WO | 2010/033786 A2 | 3/2010 |
| WO | 2010/065855 A1 | 6/2010 |
| WO | 2011/005327 A1 | 1/2011 |
| WO | 2013/086321 A1 | 6/2013 |
| WO | 2015/066038 A1 | 5/2015 |
| WO | 2019/240103 A1 | 12/2019 |

OTHER PUBLICATIONS

International Search Report dated Aug. 13, 2019 received in PCT/JP2019/022994.

International Search Report dated Aug. 13, 2019 received in PCT/JP2019/022995.

* cited by examiner

BONE PLATE AND BONE PLATE KIT

CROSS-REFERENCE TO RELATED APPLICATIONS

This is a continuation of International Application PCT/JP2019/022994, with an international filing date of Jun. 10, 2019, which is hereby incorporated by reference herein in its entirety.

TECHNICAL FIELD

The present invention relates to a bone plate and a bone plate kit.

BACKGROUND ART

A bone plate and a bone plate kit are known (for example, see Patent Literatures 1, 2, and 3).

In gonarthrosis, when, for example, arthrodial cartilage between the patella and femur is damaged, osteotomy is justified. In such surgery, the bone is cut (or fractured), bending of the bone is corrected, and the bone is fixed by using a bone joining plate until the bone is united. When there is a large gap between the plate and the bone, fixing cannot be performed successfully. In such a case, typically, an operation is performed such that a bone screw having no thread on the head is screwed into the plate to reduce the distance between the bone-cut faces or the bone-fracture faces or to apply pressure while pressing the plate against the bone.

Patent Literature 1 discloses an oblong screw hole including a portion having an unthreaded recess capable of accepting a screw with a spherical head, and a portion to which a screw with a conically threaded head can be fixed.

Patent Literature 2 shows that, when a screw with a threaded head is inserted into an oblong screw hole so as to pass through a position close to an unthreaded edge of the screw hole, the head moves, and the screw becomes locked.

Patent Literature 3 shows a screw-hole structure in which the central axis of a seating face that receives the head of a screw for applying pressure is not aligned with the central axis of a screw hole, and suggests a structure intended to move a bone plate in the longitudinal direction by inserting the screw.

CITATION LIST

Patent Literature

{PTL 1} The Publication of Japanese Patent No. 4162408
{PTL 2} The Publication of Japanese Patent No. 4979712
{PTL 3} Japanese Translation of PCT International Application, Publication No. 2007-507296

SUMMARY OF INVENTION

An aspect of the present invention is a bone plate having an upper face, which is not to be in contact with bone, a lower face, which is to be in contact with the bone, and a plurality of holes arranged to receive bone screws and connecting the upper face and the lower face. In at least one of the holes, a portion of an edge, on the upper face, of the hole is formed so as to be raised in the form of a protrusion higher than the upper face around the hole.

DESCRIPTION OF EMBODIMENTS

A bone plate 2 and a bone plate kit 1 according to an embodiment of the present invention will be described below with reference to the drawings.

Figure 1:
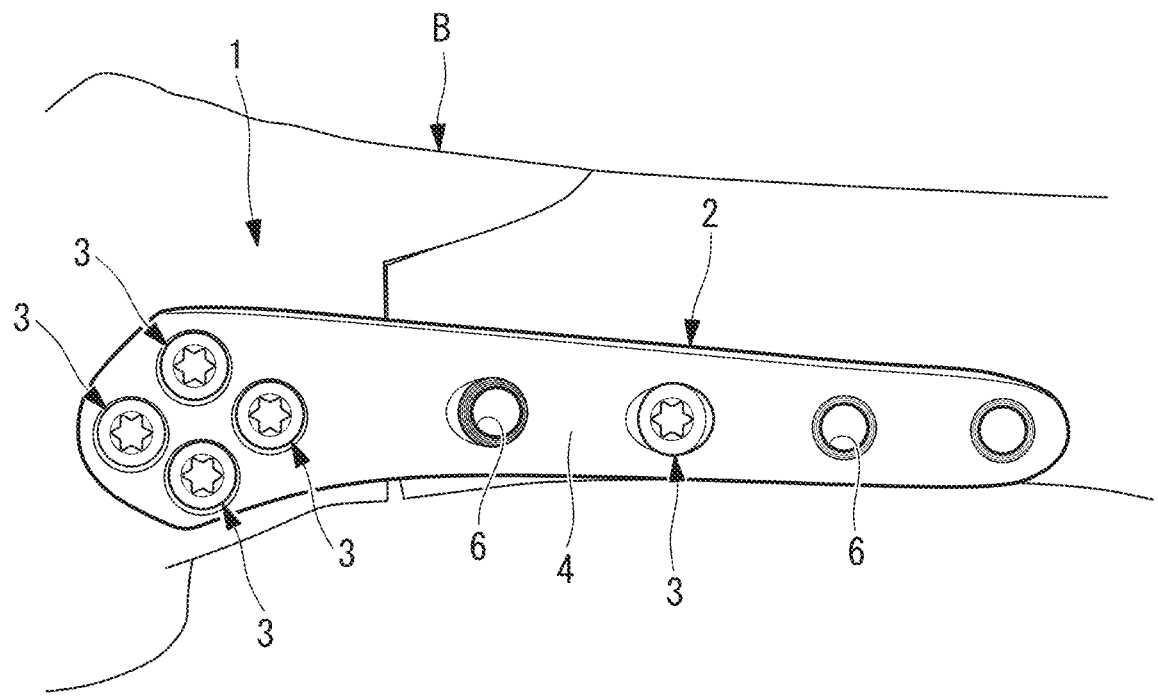
FIG. 1 is a perspective view showing a part of a bone plate kit according to an embodiment of the present invention.
Figure 2:
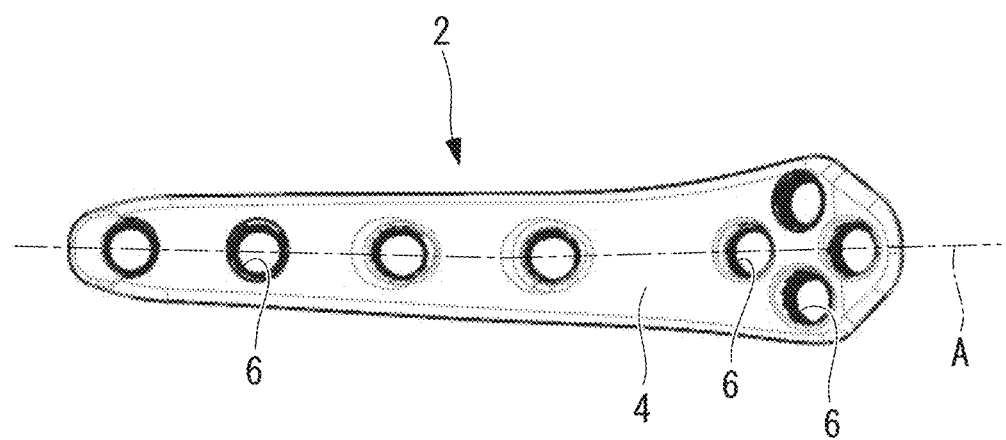
FIG. 2 is a plan view showing a bone plate provided in the bone plate kit in FIG. 1.
Figure 3:
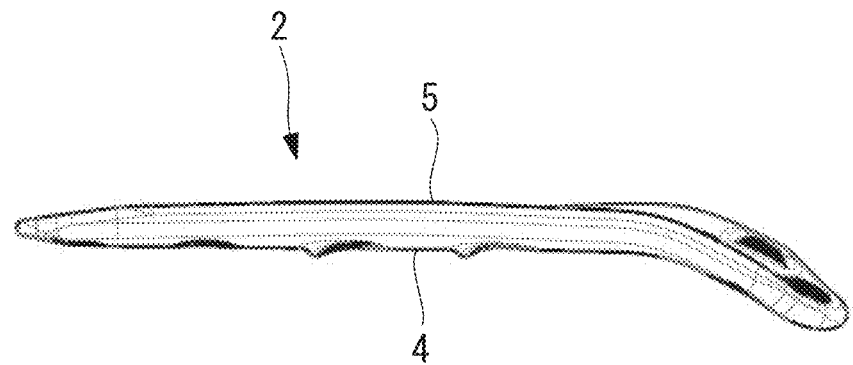
FIG. 3 is a side view of the bone plate in FIG. 2, as viewed in a direction perpendicular to the longitudinal axis.
Figure 4:
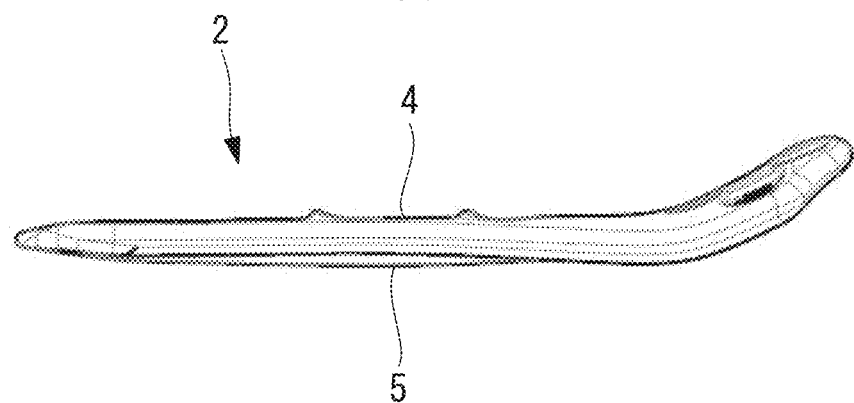
FIG. 4 is another side view of the bone plate in FIG. 2, as viewed in another direction perpendicular to the longitudinal axis.
Figure 5:
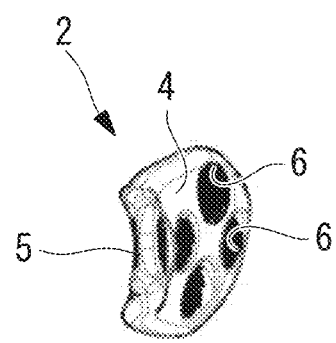
FIG. 5 is a side view of the bone plate in FIG. 2, as viewed in the longitudinal axis direction.
Figure 6:
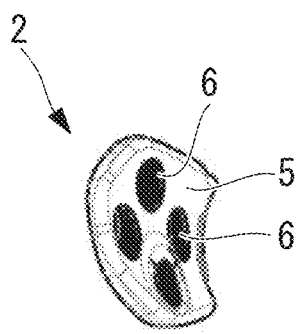
FIG. 6 is another side view of the bone plate in FIG. 2, as viewed from another side in the longitudinal axis direction.
Figure 7:
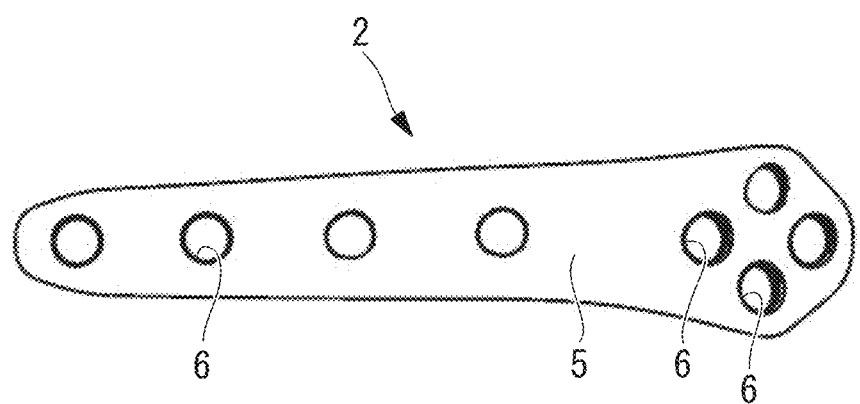
FIG. 7 is a bottom view of the bone plate in FIG. 2.

As shown in FIG. 1, the bone plate kit 1 according to this embodiment includes the bone plate 2 and bone screws 3.

The bone plate 2 according to this embodiment has a shape as shown in FIGS. 2 to 7.

The bone plate 2 has a longitudinal axis A and has an upper face 4, which is to be in contact with a bone B, and a lower face 5, which is to be in contact with the bone B. The bone plate 2 also has a plurality of screw holes (hole) 6 arranged to receive the bone screws 3 and connecting the upper face 4 and the lower face 5.

Considering appropriate elasticity to serve as bone joint materials, the bone plate 2 and the bone screws 3 are desirably made of a biomedical material (titanium, titanium alloy, stainless steel, cobalt chrome alloy, PEEK material, or polylactic acid).

The reference thickness of the bone plate 2 is desirably from 1 mm to 5 mm, and more desirably, from 2 mm to 4.5 mm. The screw holes 6 are desirably from 2 mm to 8 mm at the central portion, and more desirably, from 3 mm to 6 mm.

Figure 8:
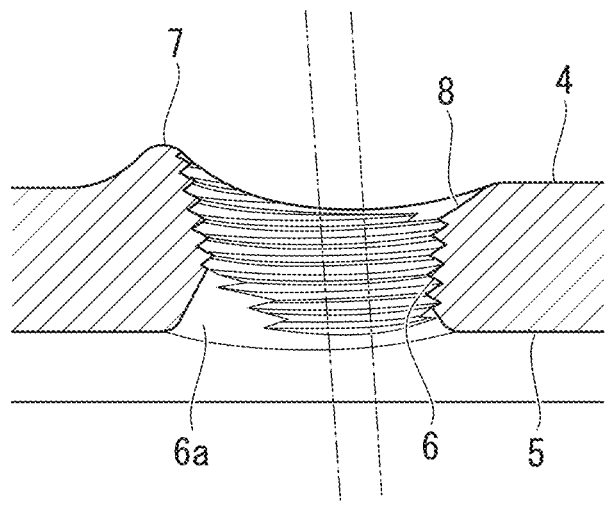
FIG. 8 is a vertical cross section showing a screw hole provided in the bone plate in FIG. 2.

As shown in FIG. 8, a protrusion 7 formed by raising a portion of an edge so as to be higher than the other portion, and a recess 8 formed by indenting another portion of the edge so as to be lower than the other portion are formed on the edge of the screw hole 6, and the periphery thereof, in the upper face 4. The edge of the screw hole 6, and the periphery thereof, in the lower face 5 have a chamfer extending in the longitudinal axis A direction.

The height of the protrusion 7 from the edge of the other portion is desirably from 0.5 mm to 3 mm, and more desirably, from 1 mm to 2 mm.

Meanwhile, the depth of the recess 8 from the edge of the other portion is desirably from 0.5 mm to 3 mm, and more desirably, from 1 mm to 2 mm.

The protrusion 7 may be provided in a C shape on the edge of the screw hole 6, and periphery thereof, and it is desirable that the protrusion 7 be provided over the area from 30° to 290°, and most desirably, from 60° to 180°, around the center of the screw hole 6.

Figure 9:
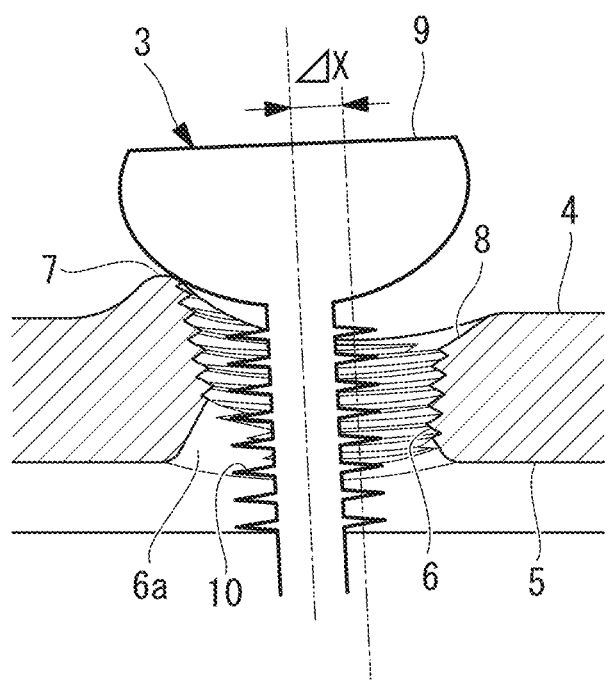
FIG. 9 is a vertical cross section for describing the principle of applying pressure to bone-fracture faces with the bone plate kit in FIG. 1.
Figure 10:
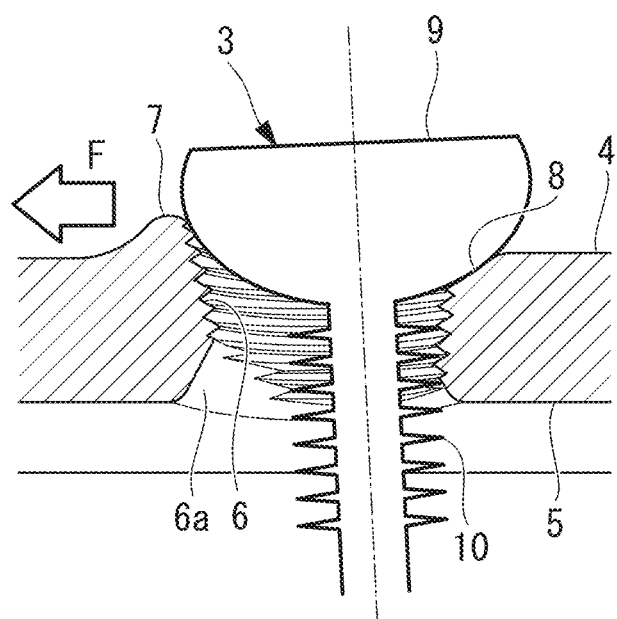
FIG. 10 is a vertical cross section showing a state in which pressure is generated by tightening the bone screw, from the state in FIG. 9.

The recess 8 in the screw hole 6 needs to have a curvature capable of accepting a pressure-applying bone screw 3. As shown in FIGS. 9 and 10, the head 9 of the pressure-applying bone screw 3 is formed in a spherical shape with no male thread and can be accommodated in the screw hole 6 so as to be supported at at least three points, namely, the recess 8, the protrusion 7, and the edge around the hole 6 and between the recess 8 and the protrusion 7.

The recess 8 and the protrusion 7 are desirably provided in the longitudinal axis A direction of the bone plate 2. When pressure is to be applied, the bone plate 2 is placed on the bone B in a state in which the protrusion 7 is located on the opposite side of the bone-fracture face from the recess 8. From the standpoint of controlling the moving direction of the bone plate 2, when the bone plate 2 is curved around the longitudinal axis A direction, and the screw holes 6 are not arranged on the central axis of the bone plate 2, the recess 8 and the protrusion 7 are desirably formed at positions located on the outer side of the central axis.

The ridge diameter of the bone screws 3 is desirably from 2 mm to 8 mm, and more desirably, from 3 mm to 6 mm. A neck of the bone screw, which is between the head 9 of the bone screw 3 and a screw portion 10 to be inserted into the bone B, is desirably greater than the groove diameter of the bone screw 3 by 0.5 mm to 4 mm in the diameter direction. This structure prevents invasion into the bone B due to excessive fastening of the bone screw 3.

One form of a basic operation process of the bone plate kit 1 according to this embodiment will be shown.

As shown in FIG. 1, after one end of the bone plate 2 is fixed to an end of the bone B with the bone screws 3, the pressure-applying bone screw 3 is inserted into the screw hole 6 located at a position on the other side of the bone fracture line.

As a result, as shown in FIGS. 9 and 10, the bone screw 3 moves the bone plate 2 by Δx in the direction in which the protrusion 7 of the bone plate 2 is pushed out, thereby applying desired pressure F to the bone-fracture faces. At this time, by fastening the bone screws 3 with male threads on the heads 9 with the other screw holes 6, which have female threads, the pressure at the bone-fracture faces is maintained even if the pressure-applying bone screw 3 in the screw hole 6 is removed. In this case, the male threads are desirably tapered.

Furthermore, when the pressure at the screw hole 6 is insufficient, pressure-applying bone screws 3 are inserted into a second screw hole 6 and a third screw hole 6 provided in the bone plate 2. By doing so, desired pressure can be applied to the bone-fracture part.

Conversely, when the positional relationship between the protrusion 7 and the recess 8 is reversed, the bone-fracture faces can be separated away from each other, and thus, use in open-wedge osteotomy becomes possible.

REFERENCE SIGNS LIST

1 bone plate kit
2 bone plate
3 bone screw
4 upper face
5 lower face
6 screw hole (hole)
6a chamfer
7 protrusion
8 recess
9 head
10 screw portion
A longitudinal axis
B bone

The invention claimed is:

1. A bone plate kit comprising:
   a bone plate; and
   a plurality of bone screws,
   wherein the bone plate comprises:
      an upper face, configured to not be in contact with a bone;
      a lower face, which is to be in contact with the bone; and
      a plurality of holes each of which connects the upper face and the lower face, each of the plurality of bone screws being inserted into one of the plurality of holes,
   wherein a first hole of the plurality of holes is arranged at one end of the bone plate,
   wherein a second hole of the plurality of holes is arranged away from the first hole in a direction of a longitudinal axis of the bone plate,
   wherein a portion of an edge, on the upper face, of the second hole is formed so as to be raised in the form of a protrusion, the protrusion being higher than the upper face around the second hole, and
   wherein in a state where a first bone screw of the plurality of bone screws is inserted into the first hole to fix the one end of the bone plate to the bone, a second bone screw of the plurality of bone screws is inserted into the second hole such that the second bone screw pushes out the protrusion to apply pressure to the bone.

2. The bone plate kit according to claim 1, wherein another portion of the edge, on the upper face, of the second hole is formed having a recess lower than the upper face around the second hole.

3. The bone plate kit according to claim 2, wherein the protrusion and the recess are formed so as to oppose each other with the second hole therebetween.

4. The bone plate kit according to claim 2, wherein the protrusion or the recess are formed along the direction of the longitudinal axis of the bone plate.

5. The bone plate kit according to claim 2, wherein the protrusion is formed at a position farther from a bone-fracture line of the bone than the recess, the bone-fracture line intersecting with the longitudinal axis of the bone plate.

6. The bone plate kit according to claim 1, wherein a chamfer on an edge, on the lower face, of the second hole extends in the direction of the longitudinal axis of the bone plate.

7. The bone plate kit according to claim 1, wherein an inner wall of each of the plurality of holes has a female thread that meshes with one of the plurality of bone screws.

8. The bone plate kit according to claim 1, wherein
   each of the plurality of bone screws includes a head that is not to enter the bone, a screw portion that is to enter the bone, and a neck connecting the head and the screw portion, and
   the neck is thicker than a groove diameter of the screw portion.

* * * * *